United States Patent [19]

Jacobson

[11] 4,367,218

[45] Jan. 4, 1983

[54] ANTI-CARIES ORAL RINSE

[76] Inventor: Jerry I. Jacobson, 1853 Central Ave., Yonkers, N.Y. 10710

[21] Appl. No.: 308,432

[22] Filed: Oct. 5, 1981

Related U.S. Application Data

[63] Continuation-in-part of Ser. No. 971,930, Sep. 6, 1979, abandoned.

[51] Int. Cl.³ .................. A61K 7/16; A61K 33/06; A61K 33/10
[52] U.S. Cl. .................... 424/49; 424/154; 424/156
[58] Field of Search .................. 424/49–58, 424/154–157

[56] References Cited

U.S. PATENT DOCUMENTS

| | | | |
|---|---|---|---|
| 138,282 | 4/1873 | Phillips | 424/157 |
| 840,738 | 1/1907 | Barnard | 424/53 |
| 926,280 | 6/1909 | Morrison | 424/49 |
| 947,120 | 1/1910 | Morrison | 424/49 |
| 975,814 | 11/1910 | Westlake | 424/53 |
| 1,112,180 | 9/1914 | Westenfelter | 424/49 |
| 1,262,888 | 4/1918 | Westlake | 424/44 |
| 1,694,341 | 12/1928 | Crossley | 424/157 |
| 1,831,409 | 11/1931 | Crossley | 424/157 |
| 1,889,366 | 11/1932 | McGowan | 424/157 |
| 2,089,845 | 8/1937 | Atkins | 424/49 |
| 2,128,917 | 9/1938 | Crocker | 424/49 |
| 2,778,045 | 1/1957 | Bly et al. | 424/58 |
| 2,783,179 | 2/1957 | Grote | 424/156 |
| 2,843,521 | 7/1958 | Entrekin | 424/49 |
| 3,116,208 | 12/1963 | Emond | 424/56 |
| 3,431,339 | 3/1969 | Gyarmathy et al. | 424/49 |
| 3,591,680 | 7/1971 | Greene et al. | 424/156 |
| 3,629,468 | 12/1971 | Andersen | 424/49 |
| 3,962,417 | 6/1976 | Howell | 424/56 |
| 4,132,770 | 1/1979 | Barth | 424/49 |
| 4,163,777 | 8/1979 | Mitra | 424/19 |

FOREIGN PATENT DOCUMENTS 900389  7/1962  United Kingdom .................. 424/49

OTHER PUBLICATIONS

A. Ph. A. Handbook of Non-Prescription Drugs, 5th Ed. (1977) pp. IV–XIII Antacids pp. 2–17, Dental Products pp. 248–263.

*Primary Examiner*—Shep K. Rose

[57] ABSTRACT

An oral rinse composition useful in the treatment and prevention of dental caries, which comprises an aqueous composition of a combination of alkali metal carbonates, and alkali metal bicarbonates, which composition must be employed by the patient being treated in a daily regimen over an extended period of time.

11 Claims, No Drawings

ANTI-CARIES ORAL RINSE

This application is a continuation-in-part application of my previously filed copending application, Ser. No. 971,930, filed Sept. 6, 1979, now abandoned.

This invention relates to a novel oral rinse which is useful for the prevention, treatment and cure of cavities. More particularly, my invention relates to a novel aqueous composition which, when employed in a specific daily regimen as an oral rinse, may be useful in the prevention and treatment of dental caries. Even more particularly, I have discovered that the novel composition of this invention if used by the patient being treated, in a specific manner as an oral rinse in strict accordance with a prescribed daily regimen over an extended period of time will be useful in the prevention or treatment of the patient's dental caries.

I have discovered that an oral rinse comprised of a combination of a (1) dihydroxy aluminum alkali metal carbonate; (2) alkali metal bicarbonate and (3) alkali metal carbonate in an aqueous medium is effective in the practice of this invention. More specifically, I have discovered that when a dihydroxy aluminum alkali metal carbonate, such as dihydroxy aluminum sodium carbonate or dihydroxy aluminum potassium carbonate, and alkali metal bicarbonate, such as, calcium or barium carbonate are combined in the specific ratios required by this invention in an aqueous composition, there is provided an oral rinse of superior properties. Even more specifically, I have discovered that a most preferable embodiment of this invention is obtained when dihydroxy aluminum sodium carbonate; sodium bicarbonate and calcium carbonate are admixed with water to obtain the preferred oral rinse of this invention.

In the practice of this invention it has been found that the ingredients comprising the oral rinse composition must be admixed in amounts in accordance with very strict limitations. In the most preferred embodiment of this invention I have discovered that the ingredients thereof must be admixed in accordance with the following ratios by weight:

| Ingredient | Parts by Weight |
| --- | --- |
| Dihydroxy Aluminum Sodium Carbonate | 20.04 |
| Sodium Bicarbonate | 15.00 |
| Calcium Carbonate | 19.50 |
| Water | 2000 |

In the event other active ingredients are employed in the practice of this invention, they must be employed in the equivalent ratios by weight as those enumerated hereinabove.

In addition to the foregoing, the final composition of the oral rinse of this invention prior to use by the patient, will have a pH of from 8.0 to 9.4, depending upon how well the composition is shaken by the patient before ingestion. Thus, the pH of the final composition of this invention can be adjusted according to the needs of the patient within the above noted range by the extent to which the composition is shaken prior to use. It is an objective of this invention to obtain and sustain a constant pH of 7.0 to 7.2 in the patient's mouth with the use of the instant oral rinse. Thus, in order to achieve this result, the pH of the oral rinse may be adjusted before each use by the patient depending upon what pH will be needed to adjust the patient's oral pH to the desired level.

The oral rinse of this invention may be employed by the patient in accordance with a regimen which will provide the desired results. I have found that most beneficial results are obtained when from about 8 to 15 ml. of the final oral rinse of this invention is taken into the mouth of the patient and without swallowing is by movement of the patient's oral musculature contacted with all parts of the patient's gums and teeth for a period of up to 30 seconds and then expectorated. This procedure should be followed by the patient at least 5 to 6 times each day of treatment. Most preferably, it is desired that the patient rinse with 15 ml. of the oral rinse composition of this invention for at least 15 seconds every 2-3 hours each day to obtain optimum results with this invention. The precise conditions under which the patient can or should optimally practice this invention, will of course depend upon the needs and condition of each patient being treated and can be precisely adjusted accordingly.

The active ingredients comprising the oral rinse of the instant invention must be pharmaceutically acceptable materials and at least meet the specifications set forth in compendiums describing such products, for example, the United States Pharmacopeoia or National Formulary or such other recognized equivalent compendium.

Although the active ingredients of the compositions of this invention may be those which specifically conform to the requirements of a compendium such as the United States Pharmacopeoia, it has also been found that the instant invention may also be satisfactorily practiced by employing commercially available materials. Thus, it has been discovered that the dihydroxy aluminum sodium carbonate which may be employed in the practice of this invention may be obtained by employing commercially available tablets sold under the tradename, "Rolaids", each such tablet providing 334 mg. of the dihydroxy aluminum sodium carbonate. Likewise, the calcium carbonate employed in the practice of this invention may be obtained by employing commercially available tablets sold under the tradename, "Tums", each such tablet providing 650 mg. of calcium carbonate. It should be understood that the selection of the source of the active ingredients employed in the practice is within the purview and knowledge of the skilled worker, although the foregoing sources all provide satisfactory results in the practice of the instant invention.

The water vehicle employed in the practice of this invention must also meet the requirements and specifications for use in the therapeutic products of this invention. Thus, the water employed in the oral rinse compositions of this invention should be distilled and non-pyrogenic, pure water. In addition, if desired the water used in the compositions of this invention may be deionized as well. From the nature and employment of the compositions of the instant invention the skilled worker can readily determine and comprehend the nature thereof and the prerequisite properties of the requirements for each of the elements thereof.

The preparation of the oral rinse compositions of this invention may be accomplished in a number of ways, which are known to and understood by the worker skilled in the art. The active ingredients of the instant invention may first be thoroughly ground to a uniform consistency so as to permit them to be easily made into a uniform aqueous composition upon the addition and admixture of the water thereto. This addition and admixing of the water may be accomplished by any method known to and usually practiced by the worker skilled in the art, for example, by continuous mixing by mechanical stirring means. Alternatively, each of the ingredients may be incorporated into the water vehicle individually prior to the addition of the next ingredient, all as is well known to the skilled worker. In addition, if desired, the ingredients of the final oral rinse compositions of this invention may be prepared by previously mixing them with a suitable organic solvent, such as ethanol, filtering the solution through a 0.1-1.0$\mu$ filter, removing the organic solvent and then adding the resultant filtrate to the water employed in the oral rinse composition. While it is also possible to add other inert ingredients to the final oral rinse composition, for example, preservatives, flavorings or colorings, without detracting from the properties thereof, it is not necessary to do so since these add nothing to the usefulness of the final composition and depending on the additive selected might even result in some detrimental property being introduced. The preparation of the final products of this invention need not be conducted under any special conditions other than those usually required in the preparation of any pharmaceutical or therapeutic product, i.e., care being taken to assure the sterility and non-pathogenicity of the premises and products produced therein, all as should be apparent to the skilled worker.

The final compositions of the instant invention in order to perform their function properly and obtain the results required must be administered to the patient over an extended period of time following the regimen and procedures hereinabove described therefore. The period of administration will vary from patient to patient depending upon the condition being treated and the results desired and may vary from as little as 6 months up to several years.

The invention may be illustrated by the following examples:

EXAMPLE 1

To 1.5 grams of calcium carbonate is admixed with stirring, 1.95 grams of sodium bicarbonate and 2.004 grams of dihydroxy aluminum sodium carbonate. When the foregoing admixture is substantially uniform, there is added 20 ml. aliquots 200 ml. of distilled water and stirring is continued until a uniform aqueous composition is obtained.

EXAMPLE 2

Six tablets of dihydroxy aluminum sodium carbonate (sold commercially under the tradename "ROLAIDS"), and three tablets of calcium bicarbonate (sold commercially under the tradename, "TUMS"), and three tablets containing 650 mg. of sodium bicarbonate each are crushed together to form a uniform powder. To the resultant powder is added in 10 ml. portions with stirring, 200 ml. of distilled, deionized water and stirring is continued until complete solution is obtained. The resultant oral rinse composition may then be used directly by the patient without any further treatment being required.

EXAMPLE 3

Oral rinse compositions prepared in accordance with the procedures set forth in Example 1 to 2 may be employed by the patient without further treatment or modification. The patient takes 15 ml. of the oral rinse into his mouth and by manipulation of the oral musculature causes the rinse to contact all parts of the mouth and teeth over a period of at least fifteen seconds at which time the patient expectorates the oral rinse composition. This procedure is then repeated once every 3 hours daily during the patient's waking hours, for a period of six months.

EXAMPLE 4

Clinical trials were conducted to establish the efficacy of the instant invention. Fifteen hundred patients, comprising children as well as adult men and women were recruited. All patients had a history of dental caries and a substantial number of patients suffered from some form of periodontal disease. The patients were recruited and placed into five test groups of 300 patients each in accordance with the clinician's evaluation of each patient's motivation to adhere to and follow the regimen of the clinical trial, as well as the evaluation of the patient's physical attributes, i.e., diet, salivation rate, oral pH, etc. The groups were then awarded an evaluation grade from 5 to 1 (highest to lowest) and each member of each group was examined and started on the study regimen. Groups 5, 4, 3 and 2 were given the oral rinse composition of Example 2 and were instructed to rinse their mouths at least once every 3 hours each day for no less than 15 seconds with about 10 ml. of the oral rinse composition, as well as maintaining the good oral hygiene habits recommended, i.e., brushing, use of fluoride water and toothpaste and dental floss.

Group 1 was used as a control group and was given a placebo rinse to employ in following the recommended study regimen. All of the patients were then followed up by periodic return visits to the clinician over a period of from 6 months to 4 years with the results obtained as set forth in Table 1 below:

TABLE 1

| Evaluation Group | Dental Caries Disease* | | Periodontal Disease* | |
|---|---|---|---|---|
| | Initial | Final | Initial | Final |
| 5 | + | — | + | — |
| 4 | +++ | + | ++ | + |
| 3 | ++++ | ++ | ++++ | ++ |
| 2 | +++++ | +++ | +++++ | +++ |
| 1 (Control) | +++++ | +++++ | +++++ | +++++ |

*+ = least
+++++ = most

The foregoing clinical trials clearly demonstrate the beneficial results obtained from the practice of the instant invention.

The foregoing Examples are merely illustrative of the invention and should not be considered limitative thereof. The invention may be contained and described within the ambit of the claims appended hereto.

It is claimed as follows:

1. An oral rinse composition useful in the treatment and prevention of dental caries which consists in combination of 2000 parts by weight of water; 19.5 parts by weight of an alkali metal carbonate, 15.0 parts by weight of an alkali metal bicarbonate and 20.04 parts by weight of a dihydroxy aluminum alkali metal carbonate.

2. The oral rinse composition of claim 1 wherein the alkali metal carbonate is calcium carbonate or barium carbonate.

3. The oral rinse composition of claim 1 wherein the alkali metal bicarbonate is sodium bicarbonate or potassium bicarbonate.

4. The oral rinse of composition of claim 1 wherein the dihydroxy aluminum alkali metal carbonate is dihydroxy aluminum sodium carbonate or dihydroxy aluminum potassium carbonate.

5. The oral rinse composition of claim 1 wherein the water is distilled water.

6. The oral rinse composition of claim 1 wherein distilled water is combined with calcium carbonate, sodium bicarbonate and dihydroxy aluminum sodium carbonate.

7. The oral rinse composition of claim 1, when shaken, having a pH or from about a 8.0 to about 9.4.

8. The method of treating and preventing dental caries which comprises a patient suffering from or wishing to prevent dental caries, oral rinsing with from 8 to 15 ml. of the oral rinse composition of claim 1, for a period of at least 15 seconds at least 5 to 6 times each day over an extended period of time.

9. The method of claim 8 wherein the pH of the oral rinse composition is from 8.0 to 9.4 and causes the mouth and saliva of the patient being treated to have a pH of 7.0 to about 7.2.

10. The method of claim 8 wherein the oral rinse composition is comprised of a combination of 2000 parts by weight of distilled water admixed with 19.5 parts by weight of calcium carbonate, 15.0 parts by weight of sodium bicarbonate and 20.04 parts by weight of dihydroxy aluminum sodium carbonate.

11. The composition of claim 1 wherein all chemical components are pharmaceutically acceptable and meet the specifications of the United States Pharmacopea.

* * * * *